(12) United States Patent
Mathis et al.

(10) Patent No.: US 8,677,513 B2
(45) Date of Patent: Mar. 25, 2014

(54) SURGICAL SLEEVE FOR GLOVE RETENTION

(75) Inventors: Michael P. Mathis, Marietta, GA (US); John Rotella, Marietta, GA (US); Ajay Yashvantrao Houde, Duluth, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1597 days.

(21) Appl. No.: 11/096,580

(22) Filed: Apr. 1, 2005

(65) Prior Publication Data

US 2006/0218694 A1    Oct. 5, 2006

(51) Int. Cl.
*A41D 27/10* (2006.01)
*A41B 7/00* (2006.01)

(52) U.S. Cl.
USPC .................................. 2/123; 2/114; 2/125

(58) Field of Classification Search
USPC ......... 2/77, 114, 123, 125, 161.8, 161.3, 162, 2/170, 901
See application file for complete search history.

(56) References Cited

U.S. PATENT DOCUMENTS

| | | | |
|---|---|---|---|
| 3,045,815 A | 7/1962 | Abildgaard | |
| 3,338,992 A | 8/1967 | Kinney | |
| 3,341,394 A | 9/1967 | Kinney | |
| 3,502,763 A | 3/1970 | Hartmann | |
| 3,542,615 A | 11/1970 | Dobo et al. | |
| 3,692,618 A | 9/1972 | Dorschner et al. | |
| 3,736,595 A * | 6/1973 | Siegmann | 2/457 |
| 3,802,817 A | 4/1974 | Matsuki et al. | |
| 3,849,241 A | 11/1974 | Butin et al. | |
| 4,041,203 A | 8/1977 | Brock et al. | |
| 4,133,624 A | 1/1979 | Heavner et al. | |
| 4,340,563 A | 7/1982 | Appel et al. | |
| 4,389,734 A | 6/1983 | Franz et al. | |
| 4,504,977 A | 3/1985 | King et al. | |
| 4,504,978 A | 3/1985 | Gregory, Jr. et al. | |
| 4,586,196 A * | 5/1986 | White | 2/114 |
| 4,789,699 A | 12/1988 | Kieffer et al. | |
| 4,937,881 A * | 7/1990 | Heise | 2/16 |
| 5,033,115 A * | 7/1991 | Bowling et al. | 2/51 |
| 5,057,368 A | 10/1991 | Largman et al. | |

(Continued)

FOREIGN PATENT DOCUMENTS

| | | |
|---|---|---|
| EP | 1170407 | 1/2002 |
| EP | 1649768 | 4/2006 |

(Continued)

OTHER PUBLICATIONS

ASTM Designation: D1894-93, "Standard Test Method for Static and Kinetic Coefficients of Friction of Plastic Film and Sheeting", Dec. 1993, pp. 455-460.

*Primary Examiner* — Alissa L Hoey
(74) *Attorney, Agent, or Firm* — Karl V. Sidor; James B. Robinson (57) ABSTRACT

A protective garment, such as a surgical gown, includes a garment body defining sleeves. A cuff may be secured at respective ends of the sleeves. A circumferentially extending coating is disposed on the sleeves beginning at the sleeve or cuff. The coating has a high friction surface such that an end of a glove pulled over the coating is inhibited from rolling or sliding back over the coating and down the sleeve. The coating may be formed of a low-tack surface modifier and may include a dye or colorant that may be used to indicate the fluid protection level of, for example, a surgical gown.

19 Claims, 6 Drawing Sheets

(56) References Cited

U.S. PATENT DOCUMENTS

| | | |
|---|---|---|
| 5,069,970 A | 12/1991 | Largman et al. |
| 5,073,436 A | 12/1991 | Antonacci et al. |
| 5,145,727 A | 9/1992 | Potts et al. |
| 5,169,706 A | 12/1992 | Collier, IV et al. |
| 5,178,931 A | 1/1993 | Perkins et al. |
| 5,188,885 A | 2/1993 | Timmons et al. |
| 5,254,391 A | 10/1993 | Davis |
| 5,272,236 A | 12/1993 | Lai et al. |
| 5,277,976 A | 1/1994 | Hogle et al. |
| 5,278,272 A | 1/1994 | Lai et al. |
| 5,306,545 A | 4/1994 | Shirayanagi et al. |
| 5,322,728 A | 6/1994 | Davey et al. |
| 5,414,867 A | 5/1995 | Bowling et al. |
| 5,444,871 A | 8/1995 | Lopez |
| 5,466,410 A | 11/1995 | Hills |
| 5,555,561 A * | 9/1996 | Plachta et al. ............... 2/457 |
| 5,561,861 A * | 10/1996 | Lopez et al. ............... 2/123 |
| 5,572,743 A | 11/1996 | Yavitz |
| 5,588,155 A * | 12/1996 | Baker et al. ............... 2/123 |
| 5,594,955 A | 1/1997 | Sommers |
| 5,628,067 A | 5/1997 | Meyer et al. |
| 5,673,433 A | 10/1997 | Rothrum |
| 5,680,653 A | 10/1997 | Mathis et al. |
| 5,693,401 A | 12/1997 | Sommers et al. |
| 5,724,674 A | 3/1998 | Covington et al. |
| 5,729,836 A * | 3/1998 | Ewing ............... 2/409 |
| 5,749,098 A * | 5/1998 | Evans ............... 2/123 |
| 5,802,609 A | 9/1998 | Garofalo |
| 5,924,130 A * | 7/1999 | Fragomeli ............... 2/16 |
| 5,948,707 A | 9/1999 | Crawley et al. |
| 6,049,907 A | 4/2000 | Palomo |
| D431,693 S | 10/2000 | Urquhart et al. |
| 6,235,659 B1 | 5/2001 | McAmish et al. |
| 6,286,144 B1 * | 9/2001 | Henderson et al. ............... 2/69 |
| 6,530,090 B1 | 3/2003 | Ambrose et al. |
| 6,601,239 B2 | 8/2003 | Drake |
| 6,665,880 B2 | 12/2003 | Poppe |
| 6,851,125 B2 | 2/2005 | Fujikawa et al. |
| 6,934,969 B2 * | 8/2005 | Schorr et al. ............... 2/51 |
| 6,941,579 B2 * | 9/2005 | Tanenbaum ............... 2/123 |
| 7,052,642 B2 * | 5/2006 | Triebes et al. ............... 264/305 |
| 7,155,746 B2 * | 1/2007 | Schorr et al. ............... 2/51 |
| 7,302,711 B1 * | 12/2007 | Tanenbaum ............... 2/162 |
| 7,685,649 B2 * | 3/2010 | Jordan et al. ............... 2/51 |
| 2001/0053643 A1 | 12/2001 | McAmish et al. |
| 2003/0118761 A1 * | 6/2003 | Triebes et al. ............... 428/35.7 |
| 2003/0118837 A1 * | 6/2003 | Modha et al. ............... 428/423.1 |
| 2003/0226191 A1 * | 12/2003 | Modha et al. ............... 2/161.7 |
| 2004/0123367 A1 * | 7/2004 | Schorr et al. ............... 2/69 |
| 2004/0219337 A1 * | 11/2004 | Langley et al. ............... 428/198 |
| 2005/0087573 A1 * | 4/2005 | Unsworth et al. ............... 223/112 |
| 2005/0106982 A1 | 5/2005 | Berrigan et al. |
| 2005/0223471 A1 * | 10/2005 | Griesbach et al. ............... 2/160 |
| 2005/0241046 A1 * | 11/2005 | Griesbach et al. ............... 2/160 |
| 2006/0085887 A1 * | 4/2006 | Palomo et al. ............... 2/59 |
| 2006/0096003 A1 * | 5/2006 | Plaatje et al. ............... 2/114 |
| 2006/0218694 A1 * | 10/2006 | Mathis et al. ............... 2/125 |
| 2006/0218697 A1 * | 10/2006 | Modha et al. ............... 2/161.7 |
| 2007/0000006 A1 * | 1/2007 | Jordan et al. ............... 2/51 |
| 2007/0000014 A1 * | 1/2007 | Rotella et al. ............... 2/114 |
| 2007/0192932 A1 * | 8/2007 | Wells ............... 2/162 |

FOREIGN PATENT DOCUMENTS

| | | |
|---|---|---|
| GB | 2237975 A | 5/1991 |
| WO | WO 01/34053 | 5/2001 |
| WO | WO 02/29146 | 4/2002 |
| WO | WO 02/32661 | 4/2002 |
| WO | WO 02/083406 | 10/2002 |
| WO | WO 03/037121 | 5/2003 |
| WO | WO 03/037612 | 5/2003 |
| WO | WO 2004/085142 | 10/2004 |

* cited by examiner

SURGICAL SLEEVE FOR GLOVE RETENTION

The present invention relates generally to protective garments for use with gloves, for example surgical gowns used with surgical gloves.

Protective garments, such as coveralls and gowns, designed to provide barrier protection to a wearer are well known in the art. Such protective garments are used in situations where isolation of a wearer from a particular environment is desirable, or it is desirable to inhibit or retard the passage of hazardous liquids and biological contaminates through the garment to the wearer.

In the medical and health-care industry, particularly with surgical procedures, a primary concern is isolation of the medical practitioner from patient fluids such as blood, saliva, perspiration, etc. Protective garments rely on the barrier properties of the fabrics used in the garments, and on the construction and design of the garment. Openings or seams in the garments may be unsatisfactory, especially if the seams or openings are located in positions where they may be subjected to stress and/or direct contact with the hazardous substances.

Gloves are commonly worn in conjunction with protective garments, particularly in the medical industry. Typically, the gloves are pulled up over the cuff and sleeve of a gown or garment. However, the interface between the glove and the protective garment can be an area of concern. For example, a common issue with surgical gloves is glove "roll-down" or slippage resulting from a low frictional interface between the interior side of the glove and the surgical gown sleeve. When the glove rolls down or slips on the sleeve, the wearer is at greater risk of exposure to patient fluids and/or other contaminants.

An additional problem associated with the use of surgical gloves is that as a result of the gloves being pulled up over the cuff and sleeve of the gown, a phenomenon known as "channeling" occurs. That is, the sleeve of the gown is bunched up under the glove as a result of pulling and rolling the glove up over the cuff and sleeve. Channels may develop along the wearer's wrist which may become accessible to patient fluids running down the outside of the sleeve of the gown. Such fluids may enter the channels and work down along the channels between the outer surface of the gown and inner surface of the surgical glove. The fluids may then contaminate the gown cuff, which lies directly against the wearer's wrist or forearm, particularly if the cuff is absorbent or fluid pervious.

Surgeons and other medical personnel have attempted to address concerns with the glove and gown interface in different ways. For example, it has been a common practice to use adhesive tape wrapped around the glove portion extending over the gown sleeve to prevent channels and roll down of the glove on the sleeve. This approach unfortunately has some drawbacks. Many of the common adhesives utilized in tapes are subject to attack by water and body fluids and the seal can be broken during a procedure. Another approach has been to stretch a rubber coating around the glove and sleeve. This practice is, however, awkward to implement and difficult to adjust or to vary the pressure exerted by the rubber coating other than by using rubber coatings of different sizes and tensions, which of course necessitates having a variety of rubber coatings available for use. Yet another approach has been to incorporate a band of elastomeric polymer on the gown around the sleeve just above the cuff to provide a surface for the glove to cling to. This approach has also proved less than completely satisfactory.

A need exists for an improved device and method for providing an effective sealing interface between a glove and sleeve of a protective garment, wherein the device is easily incorporated with the protective garment and economically cost effective to implement.

SUMMARY

The present invention provides a protective garment incorporating an effective and economical mechanism for improving the interface area between the sleeves of the garment and a glove pulled over the sleeves. The improvement inhibits the proximal end of the glove from rolling or sliding back down the garment sleeves once the wearer has pulled the gloves on. In this way, the garment according to the invention addresses at least certain of the disadvantages of conventional garments discussed above.

It should be appreciated that, although the present invention has particular usefulness as a surgical gown, the invention is not limited in scope to surgical gowns or the medical industry. The protective garment according to the present invention has wide application and can be used in any instance wherein a protective coverall, gown, robe, etc., is used with gloves. All such uses and garments are contemplated within the scope of the invention.

In an embodiment of the invention, a protective garment is provided having a garment body. The garment may be, for example, a surgical gown, a protective coverall, etc. The garment body includes sleeves, and the sleeves may have a cuff disposed at the distal end thereof. The cuffs may be formed from or include an elastic material, and may be liquid retentive or liquid impervious.

In one embodiment, the raised profile area is formed from a surface modifier material applied to the garment fabric, for example by spraying, coating, etc. This coating material may be of a type to enhance (increase) surface friction between the glove and garment. For example, the area may be coated with a low-tack adhesive material applied to the sleeve near the distal end of the sleeve or proximal end of the cuff.

In a further embodiment, it may be desirable to apply the surface modifier, particularly a low-tack material, to an area of the sleeve in a pattern that may improve the hold of the glove on the garment. This pattern may be one which would provide good frictional hold between the two items yet use less surface modifier material than complete coverage of the area would use. The term "pattern" is not meant to include the provision of a band of polymer about the sleeve in a location where it may come in contact with the glove. Gowns made according to the instant invention do not include a band of polymer around the sleeve, i.e., the sleeves are essentially free of a circumferentially extending polymeric band.

The "low-tack" material applied to the coating and/or sleeve is desirably an inherently low-tack substance with high friction characteristics so as to prevent glove roll-down while not causing the sleeves to adhere to the gown body when the gown is folded.

Embodiments of the protective garment according to the invention are described below in greater detail with reference to the appended figures.

DETAILED DESCRIPTION

Reference will now be made in detail to one or more examples of the invention depicted in the figures. Each example is provided by way of explanation of the invention, and not meant as a limitation of the invention. For example, features illustrated or described as part of one embodiment may be used with another embodiment to yield still a different embodiment. Other modifications and variations to the described embodiments are also contemplated within the scope and spirit of the invention.

Figure 1:
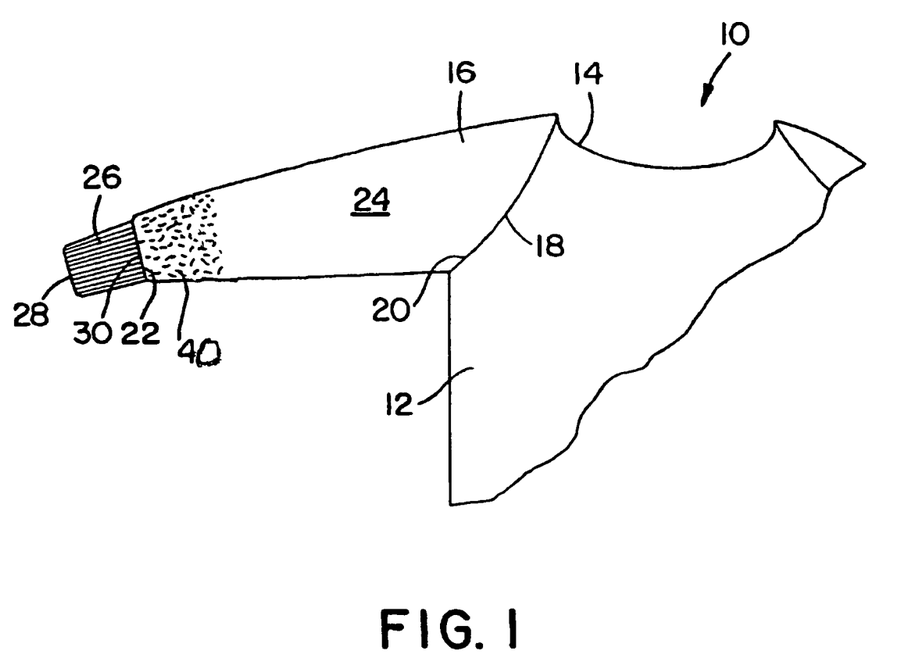
FIG. 1 is a partial side view of an embodiment of a protective garment according to the present invention.

FIG. 1 illustrates a protective garment 10 according to the invention. The garment 10 includes a main body portion 12, a neck portion 14, and sleeves 16 (one sleeve shown). The sleeves 16 may be made separately and attached at to the main body portion 12 at a seam 18 or formed as an integral component with the main body portion 12. Each sleeve 16 may include an upper or proximal end 20, a lower of distal end 22, and an exterior surface 24.

The garment 10 is depicted as a surgical gown for illustrative purposes only. The garment 10 may be any type or style of protective covering that is generally worn about the body and includes sleeves.

The terms "lower" or "distal" are used herein to denote features that are closer to the hands of the wearer. The terms "upper" or "proximal" are used to denote features that are closer to the shoulder of the wearer.

It should be appreciated that the type of fabric or material used for garment 10 is not a limiting factor of the invention. The garment 10 may be made from a multitude of materials, including nonwoven materials suitable for disposable use. For example, gown embodiments of the garment 10 may be made of a stretchable nonwoven material so that the gown is less likely to tear during donning or wearing of the gown. A material particularly well suited for use with the present invention is a three-layer nonwoven polypropylene material known as SMS. "SMS" is an acronym for Spunbond, Meltblown, Spunbond, the process by which the three layers are constructed and then laminated together. See for example U.S. Pat. No. 4,041,203 to Brock et al. One particular advantage is that the SMS material exhibits enhanced fluid barrier characteristics. It should be noted, however, that other nonwovens as well as other materials including wovens, films, foam/film laminates, and combinations thereof may be used to construct the garment of the present invention. It is also contemplated that the garment may be coated with a liquid impervious coating to prevent fluid absorption into the garment material.

The sleeves 16 may incorporate a cuff 26 attached to the distal end 22 thereof. The cuff 26 also has a distal end 28 and a proximal end 30. The configuration and materials used in the cuff 26 may vary widely. For example, short, tight-fitting cuffs made from a knitted material may be provided. The cuff 26 may be formed with or without ribs. The cuff may be formed of a liquid repellant material or a liquid retentive material. Cuffs suitable for use with garments according to the present invention are described in U.S. Pat. Nos. 5,594,955 and 5,680,653, both of which are incorporated herein in their entirety for all purposes.

Figure 2:
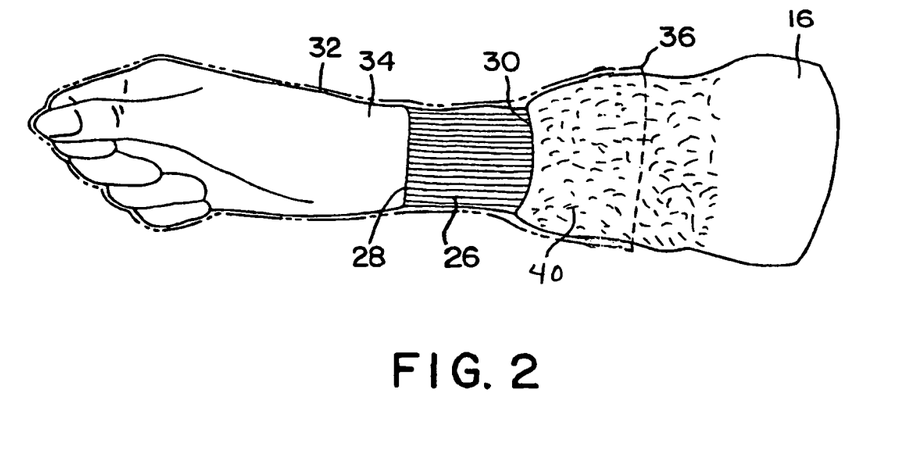
FIG. 2 is a partial side view of a garment sleeve according to an embodiment of the present invention.

As shown for example in FIG. 2, protective garments are frequently used with gloves, such as a surgical glove 32 that is pulled over the hand of the wearer and has a sufficient length so that a proximal portion of the glove 32 overlaps the cuff 26 and a portion of the sleeve 16. An interface is thus established between the glove interior surface and the exterior surface 24 of the sleeve 16 and cuff 26. This interface region preferably inhibits undesirable fluids or other contaminants from running down the sleeve 16 to the cuff 26 or hand 34 of the wearer. However, glove slippage or roll-down occurs if the frictional interface between the glove interior surface and the sleeve exterior surface is insufficient to maintain the glove in position above the cuff 26. When glove roll-down occurs, the wearer is at greater risk of exposure to contaminants, particularly during a surgical procedure.

Many types of protective gloves, particularly elastic synthetic or natural rubber surgical gloves, have a thickened bead or region at the open proximal end 36. This thickened portion or bead is intended to strengthen the glove 32 and provide an area of increased elastic tension to aid in holding the glove 32 up on the sleeve 16.

According to one embodiment of the invention, the garment 10 includes a circumferentially extending coating 40 formed on the sleeves 16 from the proximal end 30 of the cuff 26 (FIGS. 1 and 2). The coating 40 thus acts as a high friction surface against which the thickened proximal end 36 of the glove 32 contacts if the glove tends to slip down the exterior surface 24 of the glove. The coating 40 inhibits further slippage or roll-down of the glove 32.

The coating 40 may extend up the sleeve 16 a distance greater than the proximal end 36 of the glove 32 extends when the glove is normally donned. The dimensions of the coated area may vary as the size of the gown may also vary. As shown in any of FIGS. 1-6, the coated area may extend away from the cuff 26 for a distance of about 3 to 9 inches (7.6 to 22.8 cm), more particularly between about 4 and 7 inches (10.1 and 17.8 cm) and most particularly 5 inches (12.7 cm).

Figure 3:
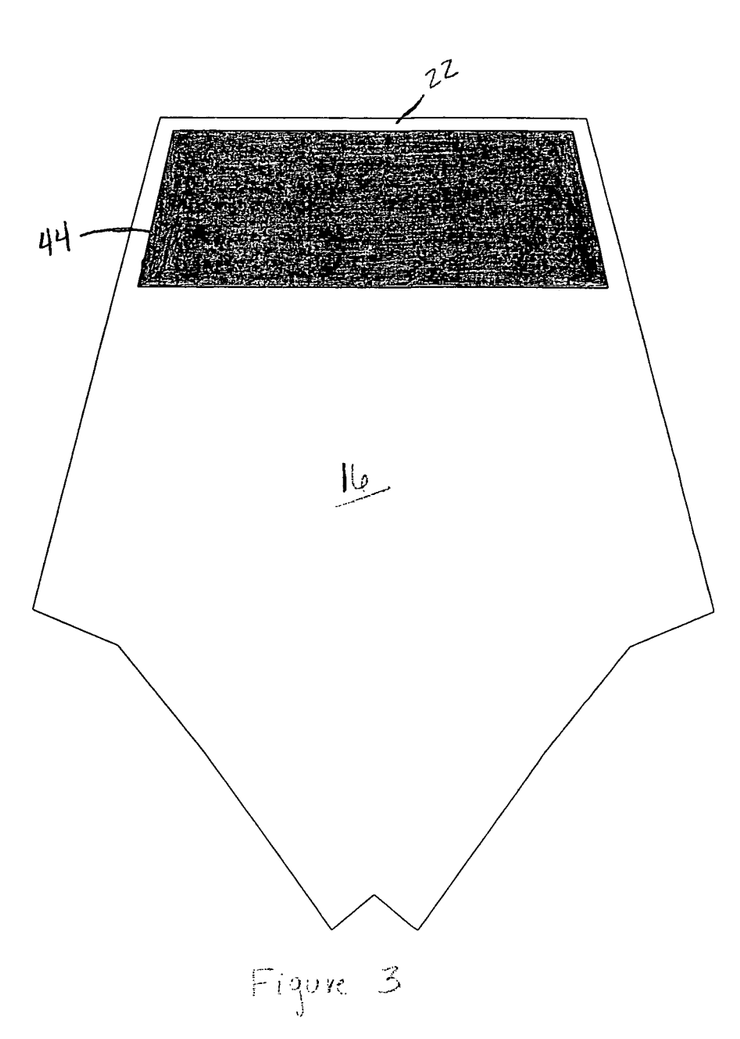
FIG. 3 is a partial perspective view of a garment sleeve having a coating according to an embodiment of the invention.
Figure 4:
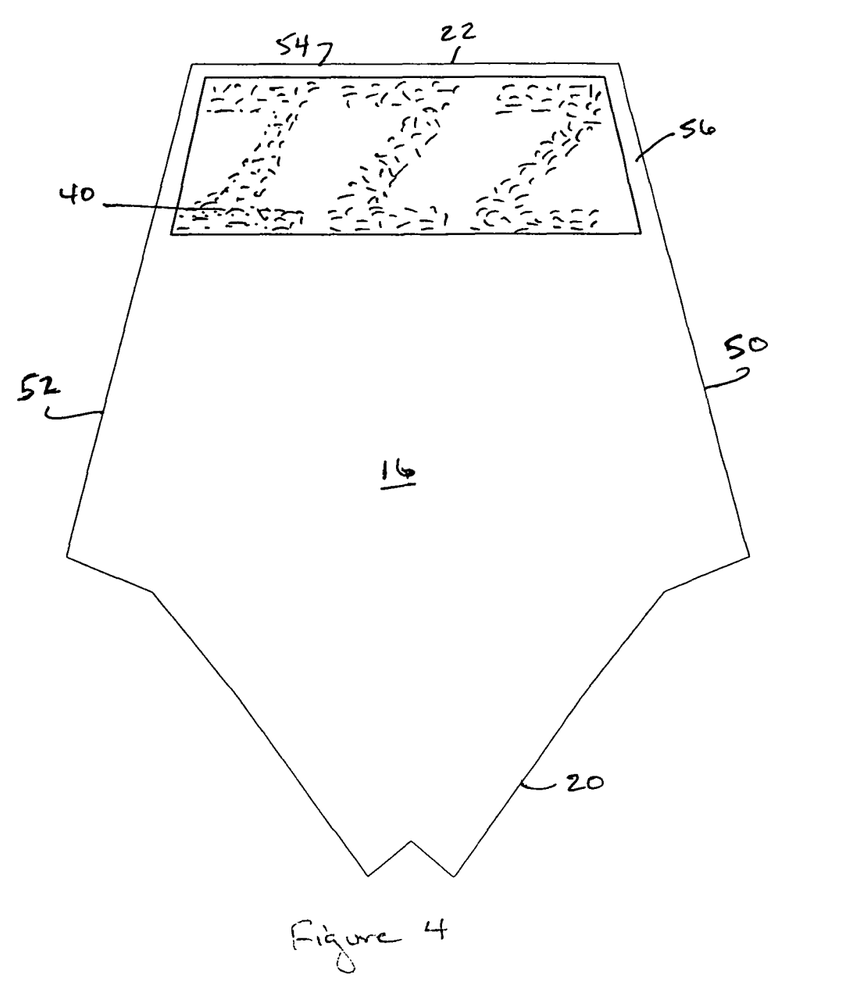
FIG. 4 is a partial perspective view of another garment sleeve having a coating deposited in a "Z" shaped configuration according to an embodiment of the present invention.
Figure 5:
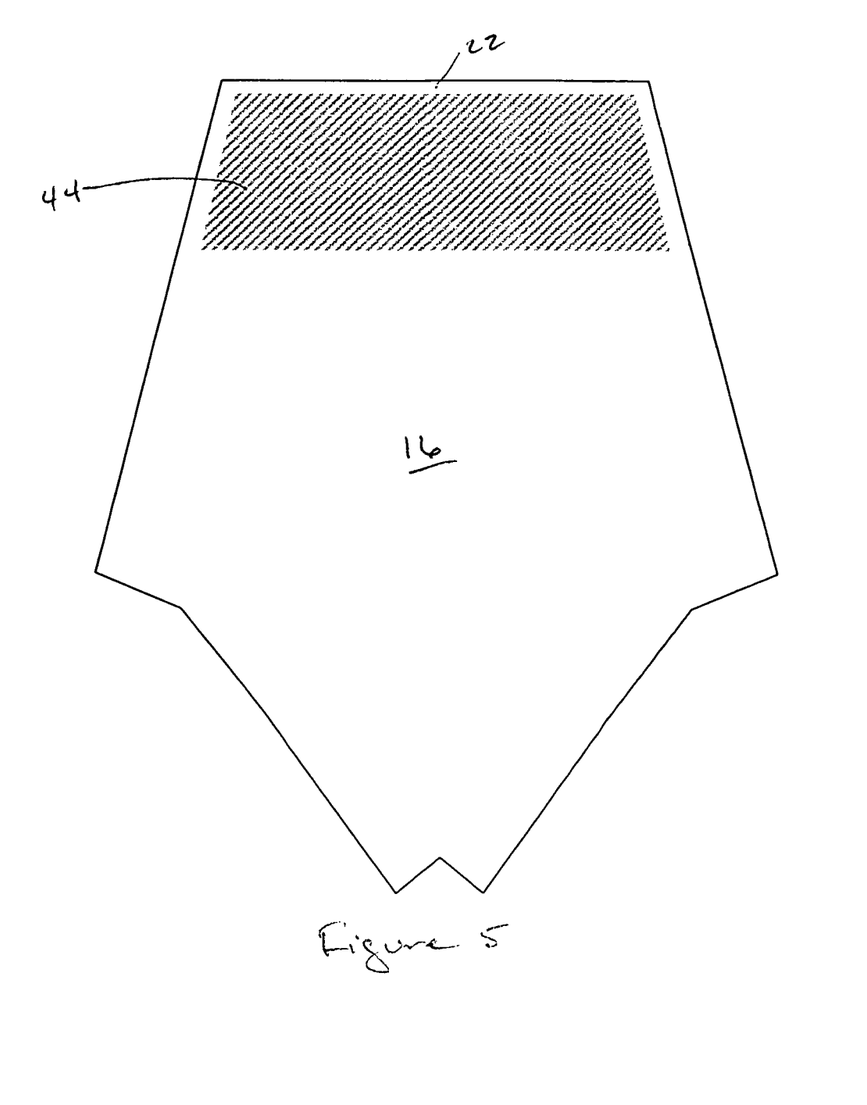
FIG. 5 is a partial perspective view of another garment sleeve having a coating deposited in a diagonal configuration according to an embodiment of the present invention.

It should be appreciated that the coating 40 can take on many different configurations. FIG. 3 shows a flat sleeve piece before it is formed into a separate sleeve 16. The sleeve 16 may be formed by bonding, for example ultrasonically, the two edges 50, 52 to each other and thereafter bonding the sleeve 16 to the main body portion 12 at the sleeve's distal end 20 to form a seam 18. The coating 40 may be continuous around the sleeve 16 though a "band" of material as described in, for example, U.S. Pat. No. 6,530,090 is not desired. While the raised profile band of the '090 patent has been found to be effective, the inventors have surprisingly found that a relatively uniform coating of a low-tack, high-friction polymer is also quite effective and lends itself more easily to modern manufacturing techniques.

Figure 6:
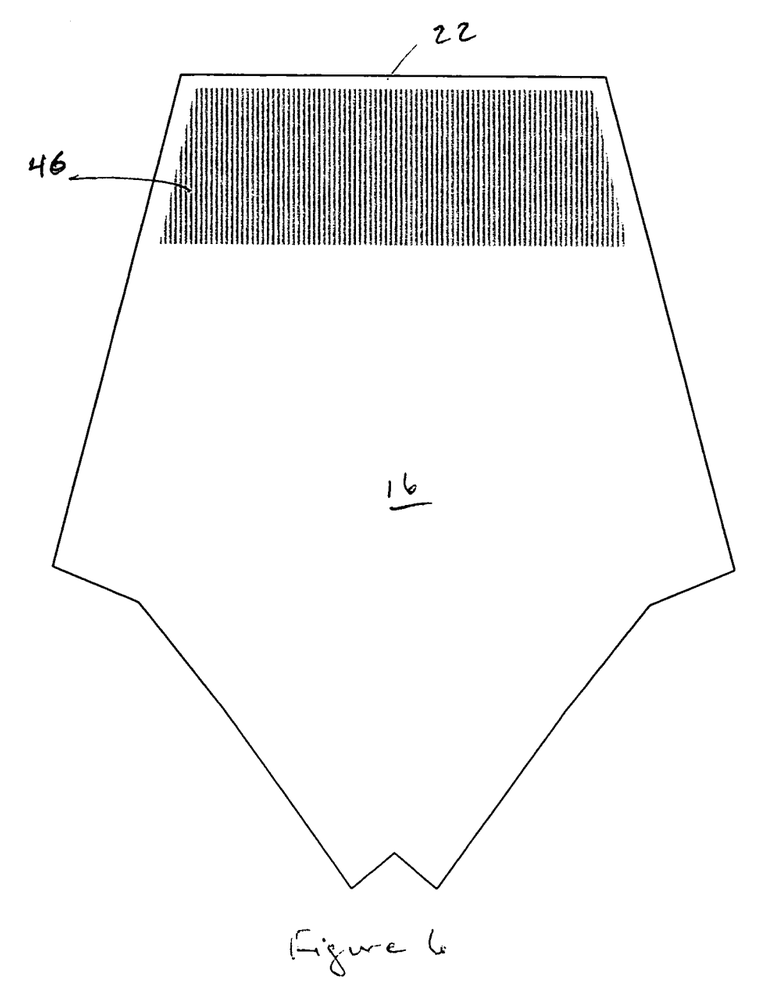
FIG. 6 is a partial perspective view of another garment sleeve having a coating deposited in a straight line configuration according to an embodiment of the present invention.

If the coating 40 interferes with the bonding or seaming process about a half inch (1.25 cm) border 56 along the edges 50, 52, 54 may be kept uncoated. If the coating 40 does not interfere with the bonding process, the half inch border 56 need not be present. The coating may alternatively be discontinuous around the sleeve 16, such as a "Z" shape arrangement (FIG. 4), a plurality of diagonal coating lines 44 (FIG. 5) or coating strips 46 extending away from the distal end 22 (FIG. 6). The particular geometric configuration of the coating 40 may vary widely so long as a generally circumferentially extending area or region is provided, with the coating being sufficient to inhibit glove slippage or roll-down.

The coating 40 may be formed on the sleeve in various known ways and from a variety of materials. For example, a surface modifier compatible with the sleeve material may be applied directly to the sleeve in a spraying, printing, slot coating, or other conventional process.

The coating 40 may be formed of an inherently low-tack material with high frictional characterisitics, such as a low-tack hot melt adhesive. This type of material increases slip resistance between the glove and sleeve 16 and may be applied directly onto the exterior surface 24 of the sleeve to form the coating 40. In general, the surface modifier could be any polymer that is sufficiently soft and pliable so as to cling to the inside surface of the glove 32. At the same time, the polymer should not have too high a tack level so as to cause the garment sleeve 16 to stick to the garment body 12 when the garment 10 is folded, hence the term "low-tack". The term "high frictional characteristics" means that the coefficient of friction of the coated fabric is higher than the same, uncoated fabric.

Polymers such as metallocene based polyolefins are suitable examples of acceptable coatings. Other suitable surface coatings include, for example, ethylene vinyl acetate copolymers, styrene-butadiene, cellulose acetate butyrate, ethyl cellulose, synthetic rubbers including, for example, Krayton® block copolymers, natural rubber, polyethylenes, polyamides, flexible polyolefins, and amorphous polyalphaolefins (APAO). A suitable commercial hot melt adhesive for the coating application is REXtac® 2115 APAO from Huntsman Polymers Corp. of Odessa, Tex. Another suitable commercial hot melt adhesive for this application is REXtac® 2215 APAO (Amorphous PolyAlpha Olefin) also from Huntsman Polymers. The polymer may be applied to the sleeve at an amount between about 5 and 50 gsm, more particularly between 10 and 30 gsm or still more particularly about 20 gsm.

Other materials may be added to the coating to provide particular characteristics. These optional materials may include, for example, dyes, pigment or other colorants to give the coated area a visually perceptible color such as yellow, green, red or blue (e.g. Sudan Blue 670 from BASF). These colors may be used to indicate the protection level accorded by the gown according to, for example, the standards of the Association for the Advancement of Medical Instrumentation (AAMI), e.g., ANSI/AAMI PB70:2003. A user would thus be able to select a gown for a surgical procedure where the sleeve color corresponded to or indicated the fluid protection level of the gown.

In order to validate the superiority of the inventive garment sleeve coating in the retention of gloves, testing was carried out on a variety of coatings and an uncoated "control" sleeve.

The control was a sleeve made from 1.7 osy (58 gsm) SMS made from polypropylene. Two samples of sleeves of the same 1.7 osy SMS material were coated with REXtac® 2115 APAO for comparison; one at an add-on rate of 10 gsm for a distance of 4 inches (10 cm) from the cuff (sample 1) and one at an add-on rate of 20 gsm for a distance of 6 inches (15 cm) from the cuff (sample 2). The sleeves were coated by a spraying process. The three sleeves were tested using human subjects and an experimental protocol designed to simulate tasks performed by medical personnel in an operating room. During and after the protocol, measurements of glove location were taken for comparison. The subjects' opinions were also solicited for a qualitative indication of gown preference. A total of 47 subjects tested the three types of gowns.

The protocol was as follows:
1. Acclimate for 10 minutes. Review Survey Questions.
2. Have the subjects wash and dry their hands using the following procedure:
    1 pump of triangle lotion soap
    15 second lather
    15 second rinse
    dry until there are no visible signs of moisture
3. Have the subject don a surgical gown.
4. Ask the subject to don gloves. Record the glove size. Remind subjects NOT to adjust gloves once the exercises have started.
Note: Be sure that the gloves are completely extended/unrolled at the cuff and snug around the wrist. Each glove should have the same starting point.
5. Mark the surgical glove in a straight line with a black marker at the bend of the wrist. Record baseline measurement from the inside of the glove bead to the wrist mark.
6. Record the measurement from the inside of the glove bead to the end of the gown cuff interface (the 'white mark'). Note whether the gown cuff interface is on the hand or the wrist. This is for both the left and right hand.
    Ask the subject to handle the following items (dry):
    at the wrist, flex hands palm down, up and down 10 times using both hands
    at the wrist, flex hands palm up, up and down 10 times using both hands
    rotate wrists to the outside 10 times using both hands
    rotate wrists to the inside 10 times using both hands.
    remove and replace stopper in test tube 5 times using each hand
    turn stop cock clockwise a full rotation 5 times using each hand
    wrap gauze 5 wraps around an artificial arm and cut gauze with scissors—unwrap, then re-wrap gauze and unwrap using other hand
    twist wrist to remove and replace top on a water bottle 5 times using each hand (exaggerate movements)
    pass a block back and forth from right hand to left hand 5 times
    twist the length of a long threaded rod 2 times using each hand
    twist the length a rope 2 times using each hand to the knot
7. Measure from the wrist mark to inside of the glove cuff (bead) and record 'After Exercise Measurement' in mm.
8. Check for flip over. Mark yes or no. If yes, measure from inside of the bead to the end of the glove fold.
9. Have the subject remove and discard gloves and gown. Wait 5 minutes and repeat with next sample.
10. After all gowns have been evaluated, have them complete Preference Survey.
11. Record on each subject's preference sheet, the order of the Concept Gown Display.
12. Change the order of the Concept Gown Display after each team has completed their Concept Preference.
    Results of the testing protocol were as follows:
    Average movement (slip-down) measured from the starting point was, for the control: 42 mm, for sample 1: 17 mm and for sample 2: 13 mm. This indicates a significant advantage for either of the coated sleeves over the uncoated sleeve.
    Qualitative survey responses were also gathered. The areas of inquiry were "cuff stays in place", "acceptability of glove slip-down", "how well to protect from fluid", "gown acceptability". The three gown sleeves were preferred by the subjects in the same order as their finish in the slip-down measurements.

In addition to the above testing, the control and sample 2 sleeves were tested for breathability using a TEXTEST FX 3300 air permeability machine from Schmid Corporation of Spartanburg, S.C., using a 38 cm² head at a test pressure of 125 Pa using 20 samples. According to the testing, the control sleeve fabric had a breathability of about 21.985 cubic feet per minute (CFM) (0.6225 cubic meter/min) and the sample 2 (coated) sleeve fabric had a breathability of about 21.020 CFM (0.5952 cubic meter/min). This indicates that, despite having a relatively heavy polymeric coating of 20 gsm, the breathability was not reduced by even 10 percent, and more particularly not even 5 percent. This indicates almost no change in the degree of comfort felt by a wearer of the coated sleeve.

Testing in order to quantify to some degree the coefficient of friction (COF) of the coated sleeve was also carried out. The control and sample 2 sleeves were tested using test method ASTM D1894 using both a glass surface and a steel surface. The data is given in the following table:

| Peak load | Glass | Steel |
| --- | --- | --- |
| Control | 92.1 | 180.5 |
| Sample 2 | 140.7 | 214.4 |

| Static COF | Glass | Steel |
| --- | --- | --- |
| Control | 0.47 | 0.92 |
| Sample 2 | 0.72 | 1.09 |

The glass and steel in the previous test were replaced with a commercial, market leading latex glove (Biogel Surgical glove by Regent) in order to gain a more realistic picture of the sleeve's performance. A number of commercially available gowns were used for comparison testing and their fabric was tested against the inside surface of the glove. The testing was done according to ASTM D1894 using the outside surface of each gown fabric, with the fabric oriented in the machine direction, as it would be orientated on a wearer.

In the table below, gown A is a commercially available gown with sleeves made from two 1.0 osy (33.9 gsm) SMS layers glued together. Gown B has a 0.6 osy (20.3 gsm) spunbond layer over a film and SMS fabric with the spunbond on the outside. Gown C has a 0.75 mil film on an SMS fabric with the film on the outside. Gown D has 1.6 osy (54.3 gsm) SMS sleeves. Gown E has 2.1 osy (71.1 gsm) spunlace sleeves.

The following table shows the test results.

|  |  | COF Peak Load | COF Static | COF Dynamic | COF Avg. Load |
| --- | --- | --- | --- | --- | --- |
| Gown A | Average | 26.846 | 0.135 | 0.114 | 22.61 |
|  | Std. Dev. | 11.992 | 0.06 | 0.056 | 11.171 |
| Gown B | Average | 44.445 | 0.223 | 0.204 | 40.564 |
|  | Std. Dev. | 4.648 | 0.023 | 0.016 | 3.178 |
| Gown C | Average | 86.257 | 0.433 | 0.404 | 80.362 |
|  | Std. Dev. | 18.303 | 0.092 | 0.082 | 16.318 |
| Gown D | Average | 47.166 | 0.237 | 0.22 | 43.842 |
|  | Std. Dev. | 4.951 | 0.025 | 0.021 | 4.23 |
| Gown E | Average | 75.974 | 0.382 | 0.343 | 68.277 |
|  | Std. Dev. | 11.48 | 0.058 | 0.054 | 10.803 |
| Sample 2 | Average | 196.658 | 1.003 | 0.774 | 151.655 |
|  | Std. Dev. | 39.746 | 0.203 | 0.146 | 28.584 |

This data shows that the sample 2 fabric had a much higher coefficient of friction in all areas than any of the competitive, commercially available gowns. Gowns having the coating according to the invention thus have a much higher ability to retain gloves and avoid slip down and roll down, and they do so without sacrificing comfort and breathability.

It should be appreciated by those skilled in the art that various modifications and variations can be made to the embodiments of the present invention described and illustrated herein without departing from the scope and spirit of the invention. The invention includes such modifications and variations coming within the meaning and range of equivalency of the appended claims.

What is claimed is:

1. A protective garment, comprising: a garment body, said garment body defining sleeves; each sleeve consisting of sleeve material, a cuff secured at the respective end of said sleeve; and a coating formed of a low-tack material with high frictional characteristics that is applied to said sleeve proximal to the cuff and extending away from the cuff for a distance of about 3 to about 9 inches, said coating providing a high friction surface such that an end of a glove pulled over said coating is inhibited from rolling or sliding back over said coating; wherein the reduction in breathability of the sleeve material having the coating is less than 10 percent when compared to the breathability of the sleeve material without the coating; each material being measured on the same automated air permeability machine using a 38 cm² head at a test pressure of 125 Pa, and wherein said sleeves are free of a circumferentially extending polymeric band having a raised profile.

2. The protective garment as in claim 1, wherein said garment body is a surgical gown.

3. The protective garment as in claim 1, wherein said coating incorporates a dye or colorant.

4. The protective garment as in claim 1, wherein said coating is-a low-tack amorphous polyalphaolefin polymer.

5. The protective garment as in claim 4, wherein said coating is a continuous coating of said low-tack material.

6. The protective garment as in claim 4, wherein said coating of said low-tack material is continuous around the sleeve.

7. The protective garment as in claim 1, wherein said coating is discontinuous around said sleeves.

8. The protective garment as in claim 1, wherein said coating is applied in a "Z" shape around said sleeves.

9. The protective garment as in claim 1, wherein said low-tack material is an adhesive.

10. The protective garment as in claim 1, wherein the reduction in breathability of the sleeve material having the coating is less than 5 percent compared to the breathability of the sleeve material without the coating and wherein the automated air permeability machine is a TEXTEST FX 3300 air permeability machine.

11. A protective garment, comprising: a garment body, said garment body defining sleeves; each sleeve consisting of sleeve material, and a coating formed of a low-tack material with high frictional characteristics comprising a low-tack amorphous polyalphaolefin polymer applied to a surface of said sleeves and extending away from a distal end of said sleeve for a distance of about 3 to about 9 inches, said coating providing a high friction surface such that an end of a glove pulled over said coating is inhibited from rolling or sliding back over said coating, wherein the reduction in breathability of the sleeve material having the coating is less than 10 percent compared to the breathability of the sleeve material without the coating; each material being measured on the same automated air permeability machine using a 38 $cm^2$ head at a test pressure of 125 Pa, and wherein said sleeves are free of a circumferentially extending polymeric band having a raised profile.

12. The protective garment as in claim 11, wherein said coating incorporates a dye or colorant.

13. The protective garment as in claim 11, wherein the coating on the sleeve is present at an amount between 10 and 30 gsm.

14. The protective garment as in claim 11, wherein said coating is continuous.

15. The protective garment as in claim 11, further comprising a cuff configured at the distal end of said sleeves, said coating disposed proximal to said cuffs.

16. A surgical gown, comprising: a gown body with sleeves; each sleeve consists of a sleeve material; a cuff secured at respective ends of said sleeves; and between about 10 and 30 gsm of a coating comprising a low-tack amorphous polyalphaolefin polymer having high frictional characteristics extending circumferentially on said sleeves proximal to said cuff and extending away from the cuff for a distance of about 3 to about 9 inches such that an end of a glove pulled over said coating is inhibited from rolling or sliding back over said coating, wherein the reduction in breathability of the sleeve material having the coating is less than 10 percent compared to the breathability of the sleeve material without the coating; each material being measured on the same automated air permeability machine using a 38 $cm^2$ head at a test pressure of 125 Pa, and wherein said sleeves are free of a circumferentially extending polymeric band having a raised profile.

17. The surgical gown as in claim 16, wherein said coating incorporates a dye or colorant.

18. The surgical gown as in claim 17, wherein said coating is continuous.

19. The protective garment as in claim 11, wherein the reduction in breathability of the sleeve material having the coating is less than 5 percent compared to the breathability of the sleeve material without the coating and wherein the automated air permeability machine is a TEXTEST FX 3300 air permeability machine.

\* \* \* \* \*